(12) United States Patent
Charlton

(10) Patent No.: US 6,960,287 B2
(45) Date of Patent: Nov. 1, 2005

(54) UNDERFILL DETECTION SYSTEM FOR A TEST SENSOR

(75) Inventor: Steven C. Charlton, Osceola, IN (US)

(73) Assignee: Bayer Corporation, Eldhart, IN (US)

( * ) Notice: Subject to any disclaimer, the term of this patent is extended or adjusted under 35 U.S.C. 154(b) by 0 days.

(21) Appl. No.: 10/153,518

(22) Filed: May 24, 2002

(65) Prior Publication Data

US 2002/0185385 A1 Dec. 12, 2002

Related U.S. Application Data

(60) Provisional application No. 60/296,910, filed on Jun. 11, 2001.

(51) Int. Cl.⁷ .................. G01N 27/327; G01N 27/333
(52) U.S. Cl. .................. 205/775; 205/777.5; 205/789; 204/403.01; 204/403.14; 204/416
(58) Field of Search .............. 204/403.01–403.14, 204/416–418; 205/775, 777.5–778, 787, 789, 792

(56) References Cited

U.S. PATENT DOCUMENTS

| | | | |
|---|---|---|---|
| 5,120,420 A | 6/1992 | Nankai et al. | 204/403.11 |
| 5,582,697 A | 12/1996 | Ikeda et al. | 205/777.5 |
| 5,628,890 A | 5/1997 | Carter et al. | 204/403.05 |
| 5,650,062 A | 7/1997 | Ikeda et al. | 205/778 |
| 5,667,653 A * | 9/1997 | Schneider et al. | 204/431 |
| 5,759,364 A | 6/1998 | Charlton et al. | 204/403.14 |
| 6,103,033 A | 8/2000 | Say et al. | 156/73.1 |
| 6,120,676 A | 9/2000 | Heller et al. | 205/777.5 |
| 6,175,752 B1 | 1/2001 | Say et al. | 600/345 |

FOREIGN PATENT DOCUMENTS

EP 0 987 544 A1 3/2000 ......... G01N/27/327

* cited by examiner

*Primary Examiner*—Alex Noguerola
(74) *Attorney, Agent, or Firm*—Alice A. Brewer

(57) ABSTRACT

A test sensor having a pair of electrodes and a reagent for electrochemically measuring the concentration of the analyte in a liquid sample. The test sensor comprises a capillary channel for collecting the liquid sample and a conductor disposed outside the capillary channel. The conductor is in fluid communication with the capillary channel. The liquid test sample is collected and moved through the capillary channel. The liquid test sample contacts the conductor when the capillary channel is substantially full to signal a full condition.

24 Claims, 3 Drawing Sheets

UNDERFILL DETECTION SYSTEM FOR A TEST SENSOR

This application claims the benefit of U.S. Provisional Application No. 60/296,910, filed Jun. 11, 2001.

FIELD OF THE INVENTION

The present invention relates generally to electrochemical biosensing for quantifying a specific component (analyte) in a liquid sample, and more particularly, to an underfill detection system for use with an electrochemical biosensor.

BACKGROUND OF THE INVENTION

It is often necessary to quickly obtain a sample of blood and perform an analysis of the blood sample. One example of a need for obtaining a sample of blood is in connection with a blood glucose monitoring system, which a user must frequently use to monitor the user's blood glucose level.

Those who have irregular blood glucose concentration levels are medically required to regularly self-monitor their blood glucose concentration level. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky, and confused. That person's judgment may become impaired and that person may eventually pass out. A person can also become very ill if their blood glucose level becomes too high—a condition known as hyperglycemia. Both conditions, hypoglycemia and hyperglycemia, are potentially life-threatening emergencies.

One method of monitoring a person's blood glucose level is with a portable, hand-held blood glucose testing device. The portable nature of these devices enables the users to conveniently test their blood glucose levels at anytime or in any place the user may be. The glucose testing device includes a test sensor to harvest the blood for analysis. Such a test sensor is described in U.S. Pat. No. 5,759,364, which is entitled "Electrochemical Biosensor." In order to check the blood glucose level, a drop of blood is obtained from the fingertip using a lancing device. The blood drop is produced on the fingertip and the blood is harvested using the test sensor. The test sensor, which is inserted into a testing unit, is brought into contact with the blood drop. The test sensor draws the blood to the inside of the test unit which then determines the concentration of glucose in the blood. Once the results of the test are displayed on a display of the test unit, the test sensor is discarded. Each new test requires a new test sensor.

One problem associated with some lancing and/or testing devices is that the requisite amount of blood for accurate test results is not always obtained. Roughly thirty percent of lances do not produce enough blood for analysis. The amount of blood obtained from each lance varies between zero and ten microliters. For an accurate result, at least two microliters of blood must be obtained. If less than this amount is obtained, the test results may be erroneous and a test sensor is wasted. More serious an issue, however, is that the user may be relying on inaccurate results when an insufficient sample volume is harvested. Obviously, because of the serious nature of the medical issues involved, erroneous results are to be avoided.

Another problem associated with conventional lancing devices is that there is no mechanism to let the user know whether the correct amount of blood has been obtained for accurate analysis. Typically, the test units come with instructions graphically illustrating the size of the blood drop required for accurate testing. However, this visual comparison is subjective and often produces inconsistent results. To insure the requisite amount of blood is produced, users often overcompensate by squeezing or otherwise manipulating their finger to produce a larger than necessary drop of blood. However, this adds time to the overall testing process and also results in an increased amount of wasted blood. It is preferable to require/obtain as little of the user's blood as possible for accurate results. Put another way, it is desirable to only obtain the required amount of blood. Often, requiring an increased amount of blood translates into a more "invasive" procedure meaning that the obtaining of the same can take more time and be more painful. Accordingly, their exists a need for a blood glucose testing device having an underfill detection system that can determine whether a correct blood sample volume has been obtained.

SUMMARY OF THE INVENTION

A test sensor having a pair of electrodes and a reagent for electrochemically measuring the concentration of the analyte in a liquid sample. The test sensor comprises a capillary channel for collecting the liquid sample and a conductor disposed outside the capillary channel. The conductor is in fluid communication with the capillary channel. The liquid test sample is collected and moved through the capillary channel. The liquid test sample contacts the conductor when the capillary channel is substantially full to signal a full condition.

The above summary of the present invention is not intended to represent each embodiment, or every aspect, of the present invention. Additional features and benefits of the present invention will become apparent from the detailed description, figures, and claims set forth below.

BRIEF DESCRIPTION OF THE FIGURES

Other objects and advantages of the invention will become apparent upon reading the following detailed description in conjunction with the drawings in which.

DETAILED DESCRIPTION OF THE ILLUSTRATED EMBODIMENTS

As discussed in the background section, test sensors are commonly used to measure the amount of glucose in a person's blood. One type of sensor for use in the determination of a person's blood glucose level is an electrochemical sensor. Such a sensor is described in commonly owned U.S. Pat. No. 5,759,364, which is incorporated herein by reference in its entirety. Other types of sensing include calorimetric sensing, which is described in commonly owned U.S. Pat. No. 5,723,284, which is incorporated herein by reference in its entirety.

Figure 1:
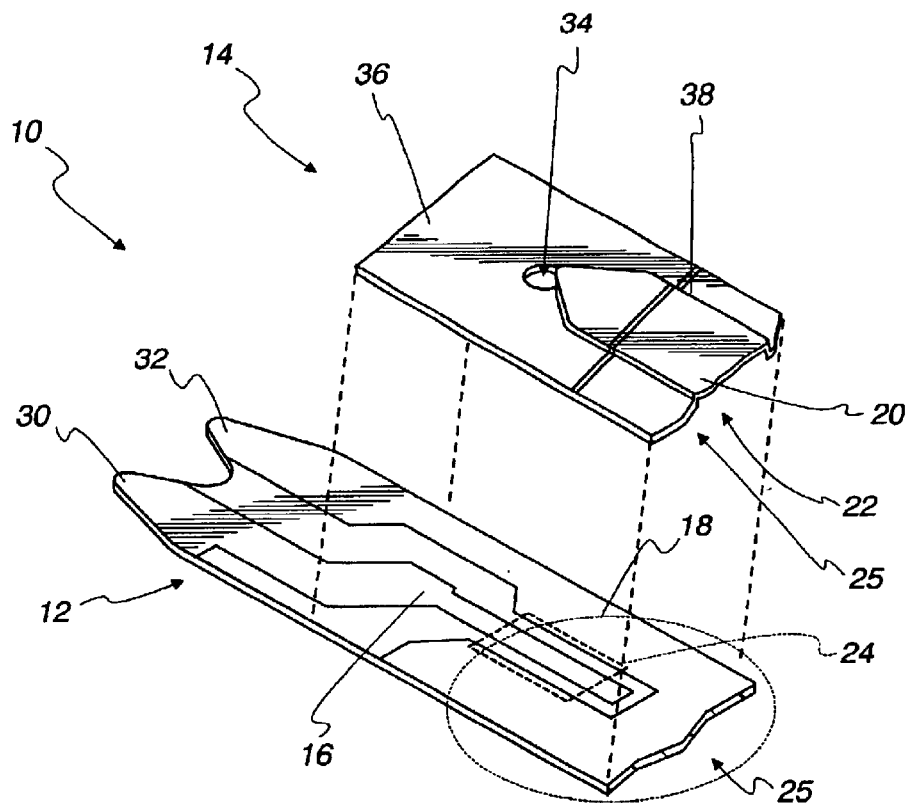
FIG. 1 is an exploded view of a lid and a base plate of a test sensor according to one embodiment of the present invention.

Referring now to FIG. 1, there is shown a test sensor 10 according to one embodiment of the present invention. The test sensor 10 includes a base plate 12 and a lid 14. The base plate 12 includes a working electrode 16 and a counter-reference electrode 18 printed on the surface of the base plate 12. The lid 14 includes a raised portion 20, the underside of which forms three side of a capillary channel 22. The base plate 12 forms the fourth side of the capillary channel 22 when the lid 14 is mated to the base plate 12. The base plate 12 also includes a reaction area or test area 24 that is generally illustrated with a dashed line. The circular area indicated by the dotted line is shown greater detail in FIG. 2.

Figure 2:
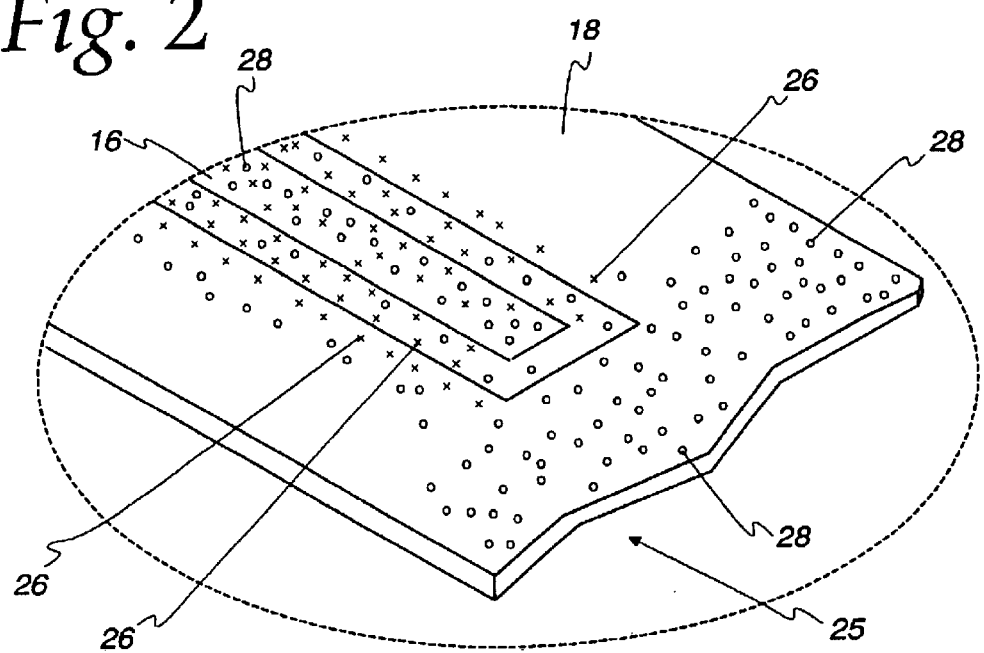
FIG. 2 is a perspective view of a sample collection end of the base plate illustrated in FIG. 1.

Referring also to FIG. 2, a sample collection end 25 of the base plate 12 is shown. The base plate 12 includes a reagent 26 incorporated into the test area 24. The reagent 26 is designed to react with the glucose in blood 28 that has moved though the capillary channel 22 to the test area 24. This reaction produces a change in current across the electrodes 16,18 that is indicative of the concentration of glucose in the sample of blood. Put another way, the reaction of glucose and the reagent creates an oxidation current at the electrodes 16,18 which is directly proportional to the user's blood glucose concentration. This current can be measured by an appropriate meter (not shown) electrically coupled to a pair of terminals 30,32 corresponding to the electrodes 16,18.

In operation, the user lances the user's fingertip to produce a sample of blood. The test sensor 10 is typically inserted into a testing device, with the sample collection end 25 exposed. The sample collection end 25 is brought into contact with the blood sample. Blood moves, via capillary action, from the collection end 25 of the sensor 10 into the test area 24 wherein the blood mixes and reacts with the reagent. As the blood moves up the capillary channel 22, displaced air vents from the capillary channel 22 via a vent hole 34. The ensuing reaction produces a change in current that is measurable across the electrodes 16,18. The change in current is measured by a meter that is coupled to the terminals 30,32.

As discussed in the background section, there exists a need for a test sensor that signals whether a sufficient sample volume has been collected by the sensor. To detect when a sufficient sample volume is collected, the test sensor is equipped with a third electrode—a signal electrode. For reasons detailed below, the signal electrode is not printed on the base plate 12 nor placed on the under surface of the lid 14 so that the signal electrode faces the capillary channel 22. Rather, a conductor 36 is formed on the outer surface of the lid 14 by coating the outer surface with a conductive material. The conductor 36 forms the terminal for the signal electrode and the working electrode 16 serves as the second electrode for the signal electrode circuit.

To form the signal electrode, the vent hole is placed at a distance so that the capillary channel 22, when filled, provides the necessary volume for a sufficient blood sample to be harvested. The sample has to make contact with the conductor 36 to signal a full condition. When a sufficient volume of blood moves though the capillary channel 22 into the vent hole 34, the blood contacts the conductor 36 to form a conductive path between the conductor 36 and the working electrode 16. The formation of the conductive path indicates that a sufficient sample volume is present for accurate testing. According to one embodiment, this path can be part of a circuit coupled to an LED which is illuminated when the conductive path is formed. Thus, the user is informed that the requisite volume of blood has been collected.

In order to ease the manufacturing of the test sensor 10, and more specifically the lid 14 having the conductor 36, the entire lid 14 is coated with the conductive coating. A line 38 is scribed in the conductive coating to electrically isolate the conductor 36 from a sample collection end 25 of the lid 14. When harvesting a sample of blood, the lid sample collection end 25 (as well as the base plate collection end 25) contact the blood sample. If the lid sample collection end 25 was not isolated from the conductor 36, a conductive path would be formed from one of the conductors 16,18 though the capillary channel 22 to the lid sample collection end 25 which has been coated with a conductive coating. Such a conductive path would incorrectly signal that a sufficient sample has been collected.

According to one embodiment of the present invention, the conductor 36 is formed by coating the lid 14 with a film of Du Pont 7102T carbon to a dry thickness of 7 $\mu$m. The vent hole 34 has a diameter of approximately 0.050 inch (about 0.127 mm). According to another embodiment, the conductor is formed by coating the lid 14 with an aluminum film. Methods of covering the lid 14 with the conductive material include coating, sputter coating, vacuum deposition, and plating. An alternative to coating the entire lid 14 with a conductive layer followed by scoring a line 38 to electrically isolate the conductor 36 from the sample collection end 25, is to place the conductive material in only the desired area using techniques such as zone coating, zone sputtering, and printing.

As briefly mentioned above, it is undesirable to print a signal electrode on the base plate 12 because doing so would effectively increase the volume of the capillary channel 22. The capillary channel 22 is designed so that only the requisite amount of blood for accurate testing is collected by the test sensor 10. Ideally, the signal electrode would be placed at the exact level of the working electrode 16. However, this is not desirable because this arrangement would short out the working electrode 16. Therefore, the signal electrode must be spaced from the working electrode 16. The inventor has found that, due in part to printing tolerances, spacing the signal electrode away from the working electrode would require the capillary channel 22 to be approximately 0.025 inch (about 0.064 mm) longer. This in turn increases the capillary area, which translates into an increased blood sample volume. This is counterproductive because, as described in the background section, it is desirable to minimize the amount of blood required for an accurate analysis.

Also mentioned above, is that it is undesirable to print a signal electrode on the underside of the raised portion 20 of the lid 14. Due to the relatively confined capillary channel 22, the surface tension of the blood sample can retard the movement of blood from the collection end 25 of the test sensor 10 though the capillary channel 22 to the test area 24. Therefore, according to one embodiment, the underside of the raised portion 20 of the lid 14 carries a bifunctional coating that facilitates the movement of the blood though the capillary channel 22. Placing the signal electrode on the underside of the raised portion 20 of the lid 14 would impede the movement of blood to the test area and increase the overall time to conduct the test.

Figure 3:
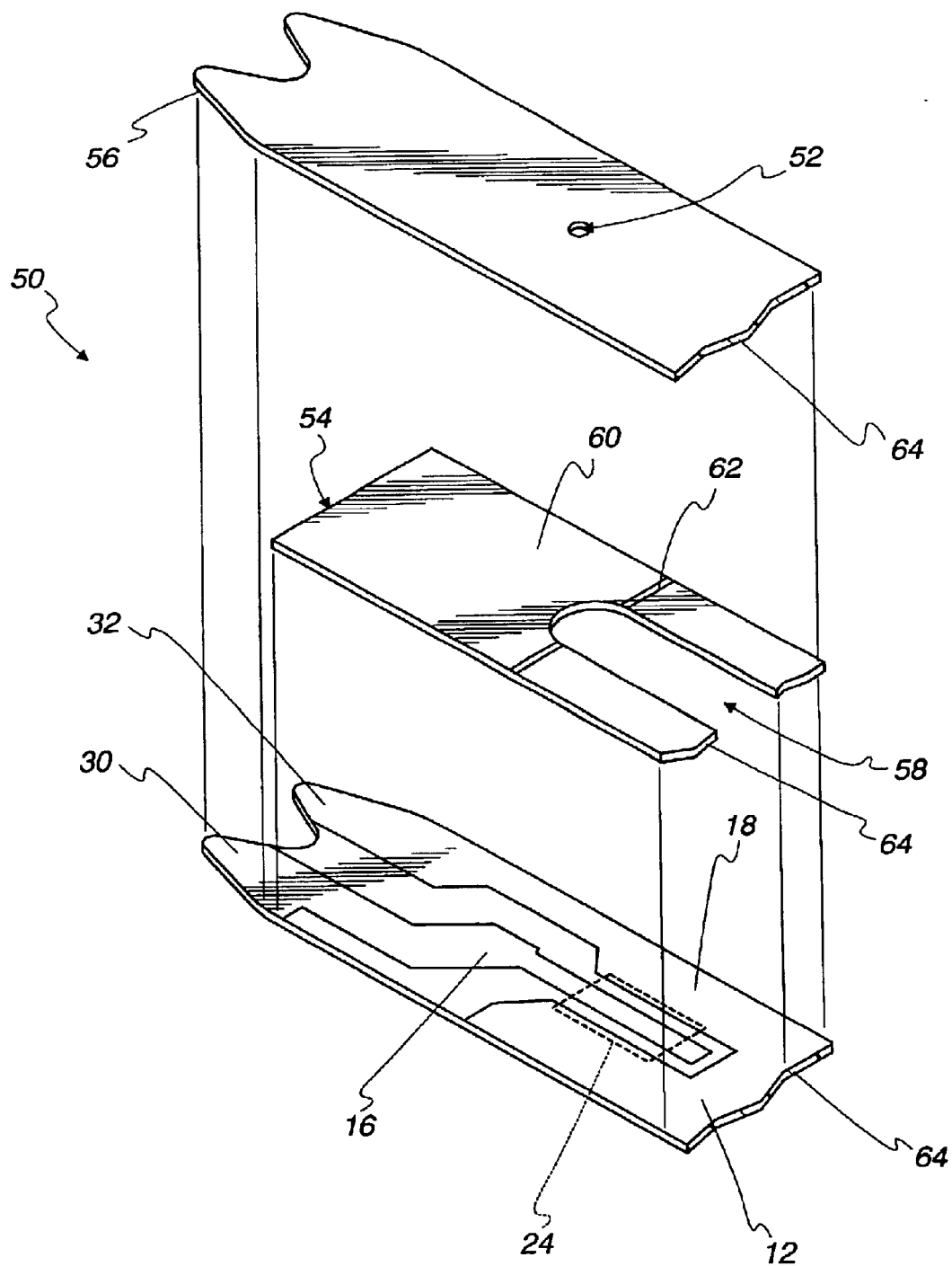
FIG. 3 is an exploded view of a lid, a spacer, and a base plate of a test sensor according to an alternative embodiment of the present invention.

Referring now to FIG. 3, an alternative embodiment of a test sensor 50 is shown. Whereas the sensor 10 shown in FIG. 1 has a "two-piece construction" (i.e., the base plate 12 and the lid 14), the sensor 50 illustrated in FIG. 3 has a "three-piece construction"—a base plate 12, a spacer 54, and a lid 56. A "three-piece construction" sensor is described in U.S. Pat. No. 5,120,420, which is hereby incorporated by reference in its entirety. The base plate 12 is similar to the base plate 12 illustrated in FIG. 1 in that it includes electrodes 16,18 electrically coupled to terminals 30,32, respectively. Further, a reagent is incorporated into the base plate 12 to react with a blood sample at the test area 24 indicated generally by dashed lines. The lid 56 includes a vent hole 52 that allows air to escape from the test sensor 50 when collecting blood.

The test sensor 50 (FIG. 3) differs from the test sensor 10 (FIG. 1) in that the lid 56 for the test sensor 50 is not deformed so as to form a capillary channel. Rather, the spacer 54 for the test sensor 50 includes a cutout which forms a capillary channel 58. The upper surface of the spacer 54 is coated with a conductive material to form a conductor 60. According to one embodiment of the present invention, the spacer is formed by first coating the spacer 54 with the conductive coating and then cutting the capillary channel 58 in the spacer 54 and conductor 60. The edges of the conductive coating are exposed to the sample in the capillary channel 58. A line 62 is scribed through the conductor 60 to electrically isolate a sample collection end 64 of the spacer 54 from the conductor 60. Once the sample fills the capillary channel 58 past the line 62, the blood sample contacts the exposed portion (i.e., the sides) of the conductor 60 to signal a full condition.

Figure 4:
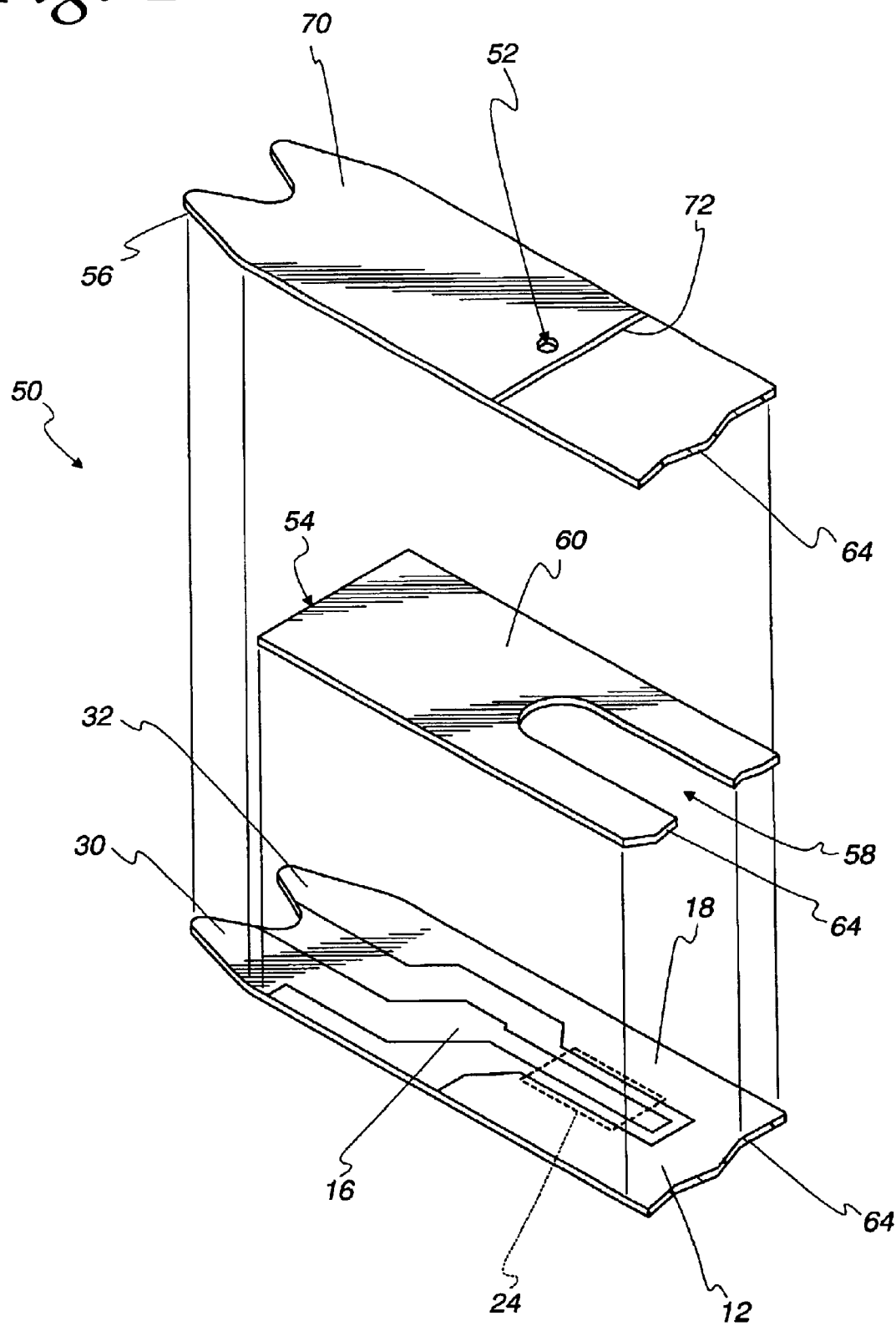
FIG. 4 is an exploded view of a lid, a spacer, and a base plate of a test sensor according to another alternative embodiment of the present invention.

Referring now to FIG. 4, according to an alternative embodiment of the test sensor 50 illustrated in FIG. 3, the lid 56 has a conductor 70 disposed thereon rather than the spacer 54. The vent hole 52 is positioned such that when blood fills the capillary channel and moves though the vent hole 52 to contact the conductor 70 conductive coating on the lid 56 a full condition is signaled. The conductor 70 is electrically isolated from the collection end 64 by a line 72 scribed through the conductive coating. This embodiment is similar to that shown in described in connection with FIGS. 1 and 2.

While the invention is susceptible to various modifications and alternative forms, specific embodiments thereof have been shown by way of example in the drawings and herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. A test sensor for measuring the concentration of an analyte in a liquid sample, the test sensor comprising:
    a base plate having a pair of electrodes and a reagent for electrochemically measuring the concentration of the analyte in the liquid sample; and
    a lid having an upper surface, a lower surface, and a conductor disposed on the upper surface, the lower surface being mated to the base plate and forming at least one wall of a capillary channel for collecting the sample, the lid having an aperture for permitting the sample to contact the conductor to signal a full condition.

2. The test sensor of claim 1 wherein the conductor is electrically isolated from a collection end of the test sample.

3. The test sensor of claim 1 wherein the conductor comprises a coating of a carbon alloy.

4. The test sensor of claim 1 wherein the conductor comprises a coating of an aluminum alloy.

5. The test sensor of claim 1 wherein the base plate includes a terminal coupled to at least one of the pair of electrodes.

6. The test sensor of claim 1 in combination with a meter adapted to measure a change in current between the pair of electrodes.

7. The test sensor of claim 1 wherein the conductor comprises a conductive coating disposed on the upper surface of the lid, and wherein a line is scribed though the conductive coating to electrically isolated a first portion of the conductive coating from a second portion of the conductive coating adjacent to the sample collection end, the line being disposed between the aperture and the collection end.

8. The test sensor of claim 1 in combination with a meter adapted to detect the presence of a conductive path between one of the pair of electrodes and the conductor.

9. A test sensor for measuring the concentration of an analyte in a liquid sample, the test sensor comprising:
    a base plate having a pair of electrodes and a reagent for electrochemically measuring the concentration of the analyte in the liquid sample;
    a spacer having a cutout forming side-walls of a capillary channel for collecting the sample;
    a lid for forming another wall of the capillary channel; and
    a conductor disposed outside of the capillary channel for contacting the sample when the capillary channel is substantially full for signaling a full condition.

10. The test sensor of claim 9 wherein the conductor is disposed on the spacer.

11. The test sensor of claim 10 wherein the conductor comprises a conductive coating disposed on the spacer, and wherein a line is scribed though the conductive coating to electrically isolate a first portion of the conductive coating from a second portion of the conductive coating adjacent a sample collection end of the test sensor.

12. The test sensor of claim 9 wherein the conductor is disposed on an outer surface of the lid.

13. The test sensor of claim 12 wherein the conductor comprises a conductive coating disposed on the lid, the lid including an aperture for permitting the sample to contact the conductor to signal a full condition, and a line scribed though the conductive coating to electrically isolate a first portion of the conductive coating from a second portion of the conductive coating adjacent to a sample collection end of the test sensor.

14. The test sensor of claim 9 wherein the conductor is electrically isolated from a collection end of the test sample.

15. The test sensor of claim 9 wherein the conductor comprises a coating of a carbon alloy.

16. The test sensor of claim 9 wherein the conductor comprises a coating of an aluminum alloy.

17. The test sensor of claim 9 wherein the base plate includes a terminal coupled to at least one of said pair of electors.

18. The test sensor of claim 9 in combination with a meter adapted to measure a change in current between the paid of electrodes.

19. The test sensor of claim 9 in combination with a meter adapted to detect the presence of a conductive path between one of the pair of electrodes and the conductor.

20. A method of determining the concentration of an analyte in a liquid sample with a test sensor, the test sensor having a pair of electrodes and a reagent for electrochemically measuring the concentration of the analyte in the liquid sample, the sensor including a capillary channel for collecting the liquid sample and a conductor disposed outside the capillary channel, the conductor being in fluid communication with the capillary channel, the method comprising:

collecting the liquid test sample;

moving the liquid test sample though the capillary channel;

contacting the liquid test sample with the conductor when the capillary channel is substantially full; and signaling a full condition when the liquid test sample has contacted the conductor.

21. The method of claim 20 further comprising reacting the regent with the analyte in the liquid sample.

22. The method of claim 20 further comprising measuring a change in current across the electrodes.

23. The method of claim 20 further comprising forming a conductive path between at least one of the pair of electrodes and the conductor when the liquid test sample has contacted the conductor.

24. The method of claim 20 further comprising detecting a conductive path between one of the pair of electrodes and the conductor.

* * * * *